(12) United States Patent
Altman

(10) Patent No.: US 6,893,422 B2
(45) Date of Patent: May 17, 2005

(54) PROTECTIVE SHIELD FOR IMPLANTED AND/OR TRANSDERMAL MEDICAL DEVICES

(75) Inventor: Sanford D. Altman, Miami Beach, FL (US)

(73) Assignee: SDA Product, Inc., North Miami Beach, FL (US)

( * ) Notice: Subject to any disclaimer, the term of this patent is extended or adjusted under 35 U.S.C. 154(b) by 86 days.

(21) Appl. No.: 10/277,481

(22) Filed: Oct. 21, 2002

(65) Prior Publication Data
US 2003/0056794 A1 Mar. 27, 2003

Related U.S. Application Data

(63) Continuation-in-part of application No. 10/232,806, filed on Aug. 28, 2002, which is a continuation-in-part of application No. 09/941,012, filed on Aug. 28, 2001.

(51) Int. Cl.$^7$ ................................................. A61M 5/32
(52) U.S. Cl. .................... 604/174; 602/41; 602/42; 602/52; 602/79; 604/171; 604/180; 128/846
(58) Field of Search .................... 128/846, 849, 128/850, 852, 853, 854, 855; 604/171, 180, 174; 602/3, 41, 42, 43, 52, 54, 57, 79

(56) References Cited

U.S. PATENT DOCUMENTS

| 3,667,469 A | 6/1972 | Marsan |
| RE29,319 E | * 7/1977 | Nordby et al. ............... 604/355 |
| 4,221,215 A | 9/1980 | Mandelbaum |
| 4,324,237 A | 4/1982 | Buttaravoli |
| 4,519,793 A | 5/1985 | Galindo |
| 4,519,797 A | 5/1985 | Hall |
| 4,636,206 A | 1/1987 | Ederati et al. |
| 4,911,151 A | * 3/1990 | Rankin et al. .................. 602/3 |

(Continued)

FOREIGN PATENT DOCUMENTS

GB 1 457 164 A 12/1976

Primary Examiner—Henry Bennett
Assistant Examiner—Camtu Nguyen
(74) Attorney, Agent, or Firm—Saliwanchik, Lloyd & Saliwanchik

(57) ABSTRACT

This subject invention is a protective shield for protecting implanted and/or transdermal medical devices, during showering, bathing, or swimming. This protective shield comprises an a protective layer including an outer pocket formed from moisture resistant adhesive material located on one side along the peripheral edge of the protective layer. In an embodiment, the outer pocket includes an inner pocket to contain and provide added protection for an implanted and/or transdermal device. In an alternate embodiment, the outer pocket includes an inner bag having an opening therethrough, where the opening is surrounded by a medical grade adhesive for attachment to a patient's skin. The medical device is inserted into the bag through the opening.

12 Claims, 7 Drawing Sheets

U.S. PATENT DOCUMENTS

| | | | |
|---|---|---|---|
| 4,969,880 A | | 11/1990 | Zamierowski |
| 5,074,847 A | | 12/1991 | Greenwell et al. |
| 5,090,406 A | | 2/1992 | Gilman |
| 5,181,274 A | | 1/1993 | DeFiore |
| 5,263,922 A | | 11/1993 | Sova et al. |
| 5,336,204 A | | 8/1994 | Matyas |
| 5,370,627 A | * | 12/1994 | Conway ..................... 604/180 |
| 5,383,893 A | | 1/1995 | Daneshvar |
| 5,415,642 A | * | 5/1995 | Shepherd ..................... 604/344 |
| 5,478,333 A | | 12/1995 | Asherman, Jr. |
| 5,495,856 A | | 3/1996 | Fentress |
| 5,605,534 A | * | 2/1997 | Hutchison ..................... 602/3 |
| 5,605,546 A | * | 2/1997 | Wolzinger et al. .......... 604/174 |
| 5,677,512 A | * | 10/1997 | Reiker ......................... 174/58 |
| 5,720,713 A | * | 2/1998 | Hutchison ..................... 602/3 |
| 5,807,341 A | | 9/1998 | Heim |
| 5,823,977 A | | 10/1998 | Dalyea |
| 5,834,093 A | | 11/1998 | Challis et al. |
| 5,843,049 A | | 12/1998 | Heilmann et al. |
| 5,885,254 A | | 3/1999 | Matyas |
| 6,095,996 A | | 8/2000 | Steer et al. |
| 6,117,111 A | | 9/2000 | Fleischmann |
| 6,124,521 A | | 9/2000 | Roberts |
| 6,222,090 B1 | * | 4/2001 | Weston ....................... 602/41 |
| 6,267,115 B1 | | 7/2001 | Marshel |
| 6,276,364 B1 | | 8/2001 | Warner |
| 6,528,697 B1 | * | 3/2003 | Knutson et al. .............. 602/54 |
| 6,540,724 B1 | * | 4/2003 | Harris ....................... 604/174 |
| 6,638,270 B2 | * | 10/2003 | Johnson ................... 604/890.1 |
| 2001/0001110 A1 | | 5/2001 | Bodenschatz et al. |
| 2001/0025153 A1 | | 9/2001 | Groitzsch et al. |
| 2001/0034505 A1 | | 10/2001 | Wilke |
| 2001/0056262 A1 | | 12/2001 | Cabiri et al. |
| 2002/0065505 A1 | | 5/2002 | Willemstyn |
| 2002/0103450 A1 | | 8/2002 | Corrales |
| 2002/0107466 A1 | | 8/2002 | Faasse, Jr. |
| 2002/0123710 A1 | | 9/2002 | Worthley |

* cited by examiner

PROTECTIVE SHIELD FOR IMPLANTED AND/OR TRANSDERMAL MEDICAL DEVICES

CROSS REFERENCE TO A RELATED APPLICATION

This application is a continuation-in-part of U.S. Ser. No. 10/232,806; filed Aug. 28, 2002, which is a continuation-in-part of U.S. Ser. No. 09/941,012, filed Aug. 28, 2001.

FIELD OF THE INVENTION

The present invention relates to a protective shield for a catheter/port and/or device that transcends from the outside of the body to the inside of the body, and more particularly to a protective shield which decreases the amount of foreign material (fluid and/or debris) presented to the catheter/port and/or device that transcends from the outside of the body to the inside of the body and to its corresponding exit site, decreasing the risk of foreign material reaching the inside of the body.

BACKGROUND OF THE INVENTION

With the improvement in healthcare over the last several decades, there is an increasing number of patients living with implanted and/or transdermal medical devices. These medical devices are being used for a variety of reasons such as dialysis, chemotherapy, alimentation, and fluid drainage, to name a few. The protection of the these devices and corresponding exit site is a significant concern for these patients, as moisture or other material can support the growth of harmful or infectious bacteria in and around the exit site.

A waterproof injection port cover is currently available that provides a waterproof adhesive around the edge of a waterproof sheet to form an area or "bubble" that does not adhere to the site that is being covered. Unfortunately, water and other debris can leak or enter into the bubble and contaminate or infect the area around the catheter.

As such, these patients ability to perform normal daily activities, such as swimming, bathing, and even showering is severally limited, and can even become prohibited for many of the patients. As a result, even when the patient begins to recover, the catheter becomes a constant reminder of their illness.

Accordingly, there remains a need for a device for protecting an implanted and/or transdermal medical device and corresponding exist site during such activities as swimming, bathing, or showering.

BRIEF SUMMARY OF THE INVENTION

The protective shield of the subject invention provides a means for protecting an implanted and/or transdermal medical device (hereinafter "medical devices") and corresponding exit site from dirt, debris, and moisture. The protective shield comprises a single protective layer that forms an outer cover over the medical device and exit site. The protective shield includes moisture resistant adhesive material disposed on the face of the protective layer for affixing the protective shield to the skin and forming a protective, watertight seal. In an embodiment, the moisture resistant adhesive material is treated with antibacterial and/or antiseptic agents to inhibit infection.

The adhesive material is disposed on the protective shield to form an outer pocket and an inner pocket. The outer pocket is formed by adhesive material that is continuously applied to the peripheral edge of the protective layer to form a protective seal. The outer pocket keeps the inner pocket dry and free from dirt and debris. The inner pocket is formed by a pattern of adhesive material disposed within the outer pocket. The adhesive material disposed within the outer pocket is configured to create an area within the outer pocket that is substantially adhesive-free and forms a continuous border around the area in which a medical device is located. The inner pocket is affixed to a patient to surround and protect the area in which the medical device is located. By way of example, the inner pocket protects an indwelling catheter and corresponding exit site from any dirt, debris or moisture that might enter into the outer pocket.

In use, the inner pocket is placed over the area in which the medical device is located and secured in place by the adhesive that forms the boundary of the inner pocket. The peripheral edges of the protective layer are placed and secured to the patient with adhesive material so that the inner pocket is encompassed within the subsequent outer pocket. The protective shield can be removed by peeling the entire protective layer from the patient's skin.

In another embodiment, the protective shield includes only the outer pocket and an inner bag located within the outer pocket. The inner bag is designed for receiving the proximal end of the catheter, having a front side and a backside, with the front side having an opening therethrough. The inner bag can be composed of materials treated with appropriate agents to inhibit the development of bacterium, fungi, viruses, and other infectious agents. The inner bag further comprises a moisture resistant adhesive material applied to the outer surface of the front side of the inner bag, substantially surrounding the opening in a continuous pattern, such that a protective seal can be formed when the inner bag is applied to the patient's skin. In an embodiment, the adhesive material is also applied to the outer surface of the back side of the inner back to affix the inner bag to the protective layer.

The protective layer that forms the protective shield of the subject invention comprises a sheet of flexible, fluid-impermeable material. The protective layer can be of any size so long as the inner pocket or the inner bag is encompassed within the peripheral edge of the protective layer. For example, the outer cover can be sized for application around a patient's waist, shoulder, or extremity. In an embodiment, where the protective shield is applied over an implanted and/or transdermal medical device (i.e., catheter or port) located on the torso and draped over a patient's shoulder, it serves as a tarp to move water away from the inner bag.

Where an inner bag is included in the outer pocket, an implanted and/or transdermal medical device is inserted into the inner bag by inserting the portion of the medical device that is outside the body though the slit in the inner bag. The portion of the medical device that is outside the body is drawn into the inner bag until the outer surface of the front side of the inner bag abuts the exit site of the medical device and surrounding area. The inner bag is secured in position by the adhesive material in contact with the patient's skin. The protective layer is positioned over the inner bag, such that the inner bag is positioned within the peripheral edges of the outer pocket. The protective layer secured in position by the adhesive material in contact with the patient's skin. The inner bag can be removed by peeling the protective layer from the patient's skin. The inner bag is gently peeled from the patient's skin and the catheter removed from the bag. The protective shield is then discarded.

An advantage of this invention is that the shield decreases the risk of foreign material reaching the inside of the body.

These and other objects, features and advantages of the present invention will be more readily understood with reference to the following detailed description, read in conjunction with the accompanying drawing figures.

All patents, patent applications and publications referred to or cited herein, or from which a claim for benefit of priority has been made, are incorporated by reference in their entirety to the extent they are not inconsistent with the explicit teachings of this specification, including: U.S. Pat. No. 4,415,642 to Shepherd, U.S. Pat. No. 4,5,495,856 to Fentress, and U.S. Pat. No. 6,222,090 to Weston.

DETAILED DISCLOSURE OF THE INVENTION

As illustrated in the figures, the protective shield 10 of the subject invention provides a means for protecting an implanted and/or transdermal medical device and corresponding exit site from dirt, debris, and moisture.

Figure 1A:
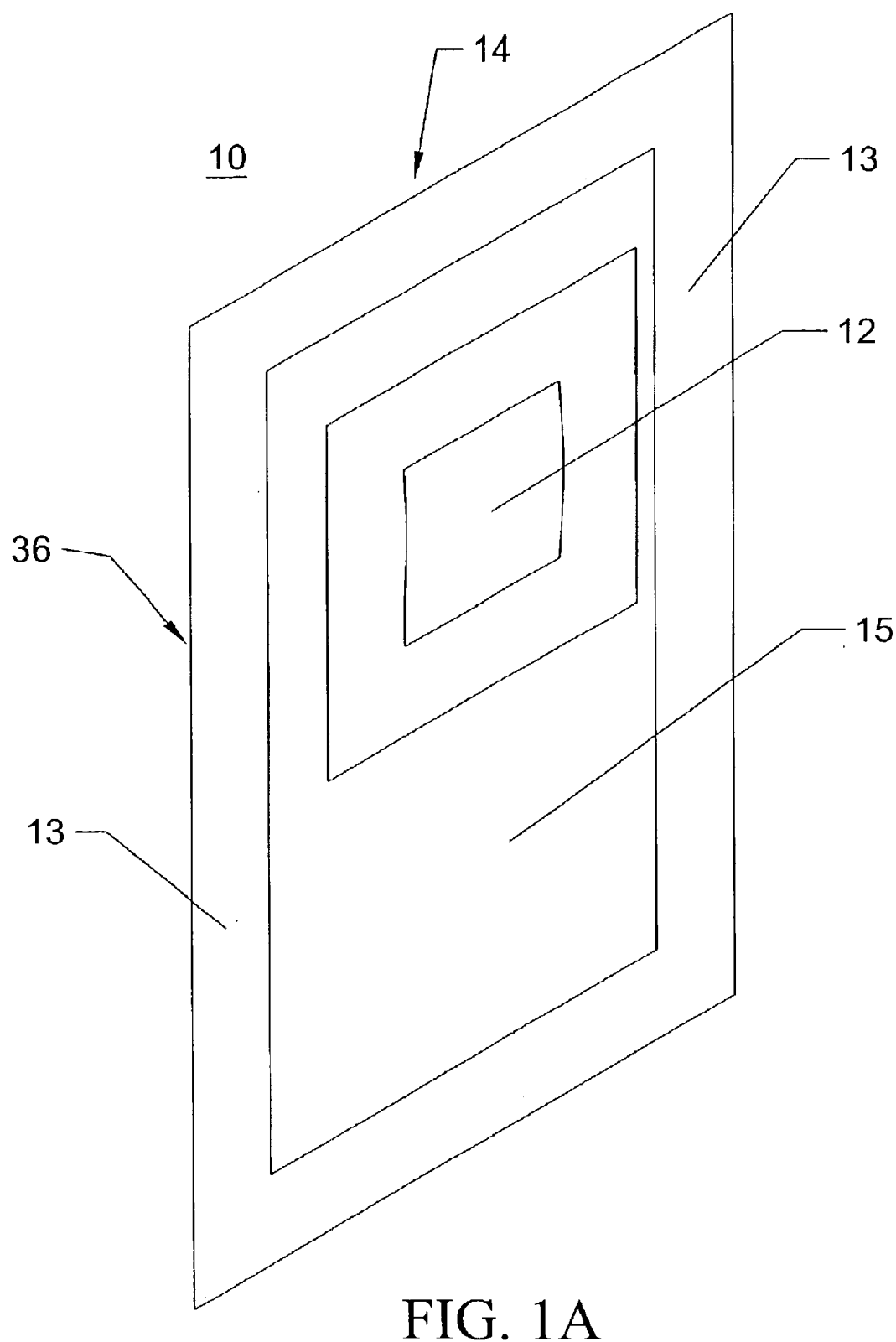
FIG. 1A depicts a perspective view of the subject protective shield, including an inner and an outer pocket.

In an embodiment, as shown in FIG. 1A, the protective shield 10 of the subject invention comprises a protective layer 14. The protective layer 14 can be made from a flexible, fluid-impermeable material capable of conforming to a patient's skin, including, but not limited to plastic, polymer, latex, or rubber. Additionally, it is desirable that the material be substantially impervious to bacterium, fungi, viruses, and other infectious agents.

The protective layer 14 has a peripheral edge 36 that when adhered to the patients skin, surrounds an inner pocket 12. A moisture resistant adhesive material 13 suitable for application to the patient's skin is applied to the peripheral edge 36 without discontinuity such that a protective seal can be formed to create an outer pocket 15 when the protective layer 14 is applied to the patient's skin. The outer pocket 15 can be of any size so long as the inner pocket 12 is encompassed within the peripheral edge 36. For example, the protective layer 14 can be sized for application around a patient's waist, shoulder, or extremity.

In an embodiment the protective layer 14 is rectangular, circular, elliptical, or any other suitable shape.

The inner pocket 12 is formed by moisture resistant adhesive material 13 disposed within the outer pocket 15 forms a continuous border around the area in which the implanted and/or transdermal medical device is located. The inner pocket 12 protects the medical device (i.e., catheter or port) and corresponding exit site from any dirt, debris or moisture that might enter into the outer pocket 15. The inner pocket 12 can be formed of any practical shape or size so that it encloses the area in which the medical device is located. The adhesive material 13 that forms the inner pocket is disposed on the protective shield 10 to form a continuous border around the area in which the medical device is located.

In an embodiment the inner pocket 12 is rectangular, circular, elliptical, or any other suitable shape.

Figure 1B:
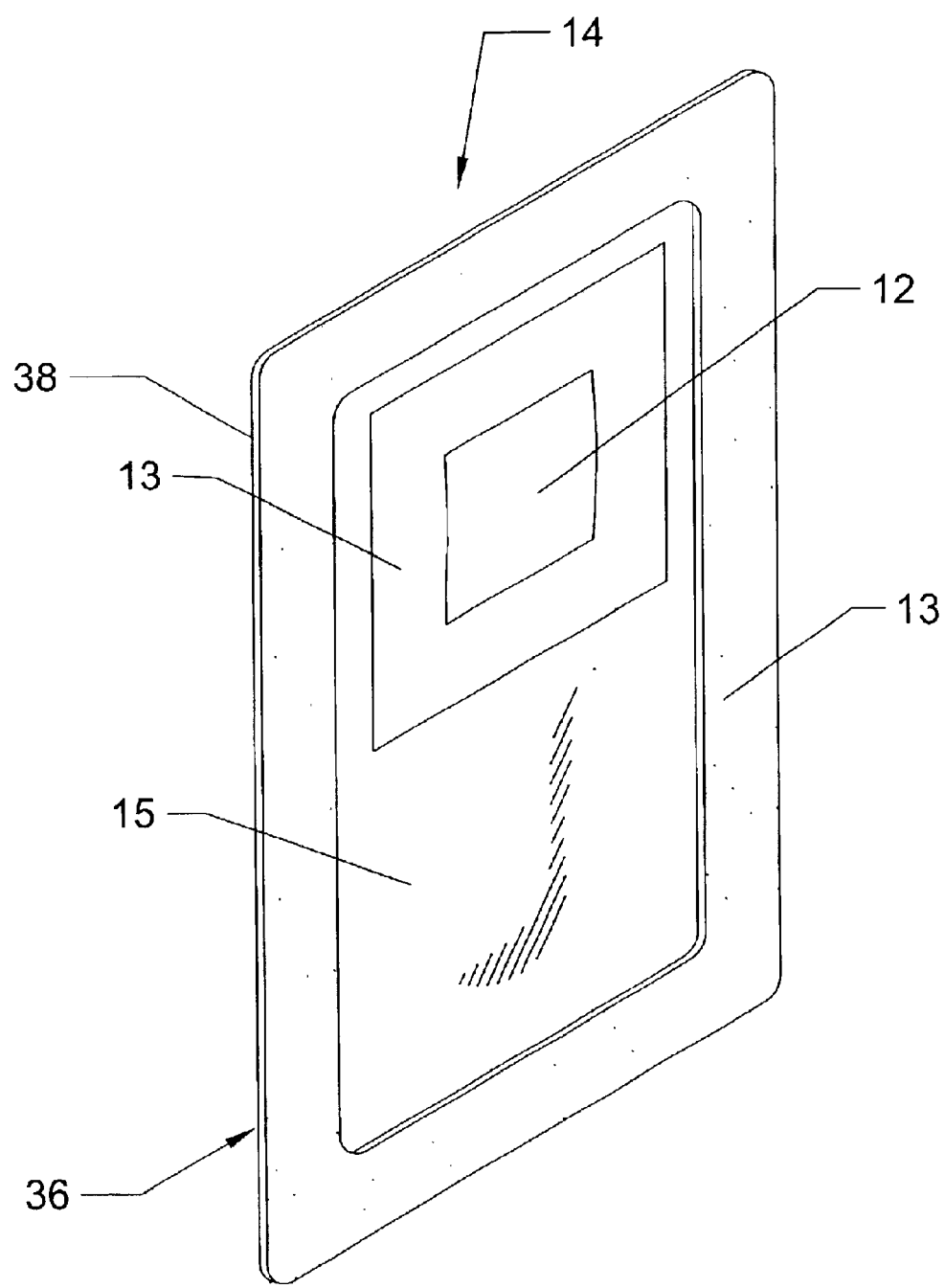
FIG. 1B depicts a perspective view of the protective layer with an annular ring.

In an alternative embodiment, as shown in FIG. 1B, the protective layer 14 further comprises an annular ring 38, where the annular ring 38 is affixed about the peripheral edge 36 of the protective layer 14. The annular ring 38 is made of a flexible material capable of conforming to the surface of a patient's skin.

According to the subject invention, a protective shield including an outer pocket and an inner pocket or inner bag provides two levels of protection. The first level of protection is afforded by the protective layer, which seals an outer pocket over the inner pocket and directs the flow of water and/or debris away from the inner pocket or inner bag. The second level of protection is the adhesive that forms the inner pocket or the inner bag applied over the medical device to the patient's skin, either of which protects and seals the medical device and the area surrounding the exit site against any moisture or debris that might have entered into the outer pocket.

Figure 2:
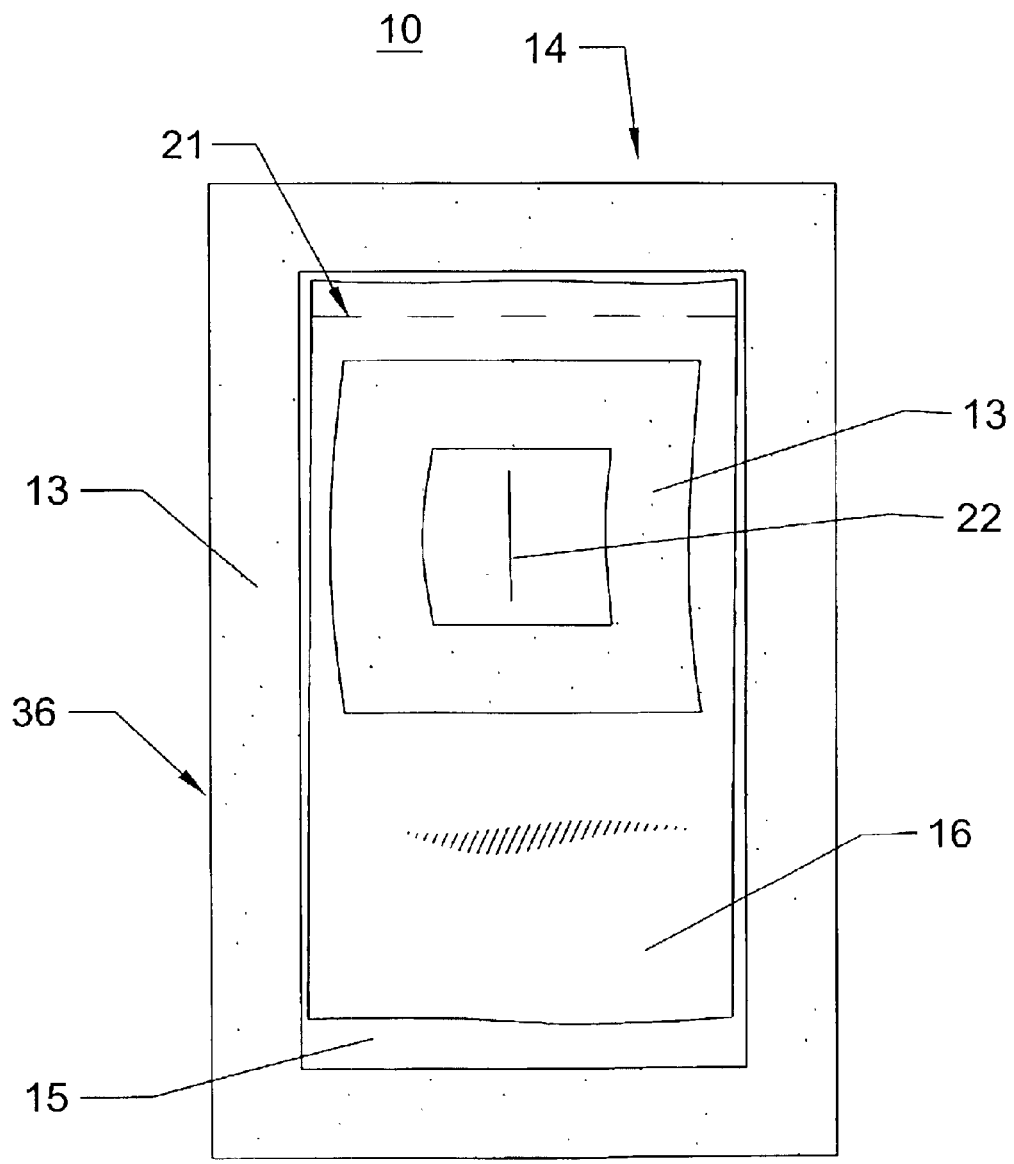
FIG. 2 depicts a perspective view of the subject protective shield, including an inner bag.
Figure 3:
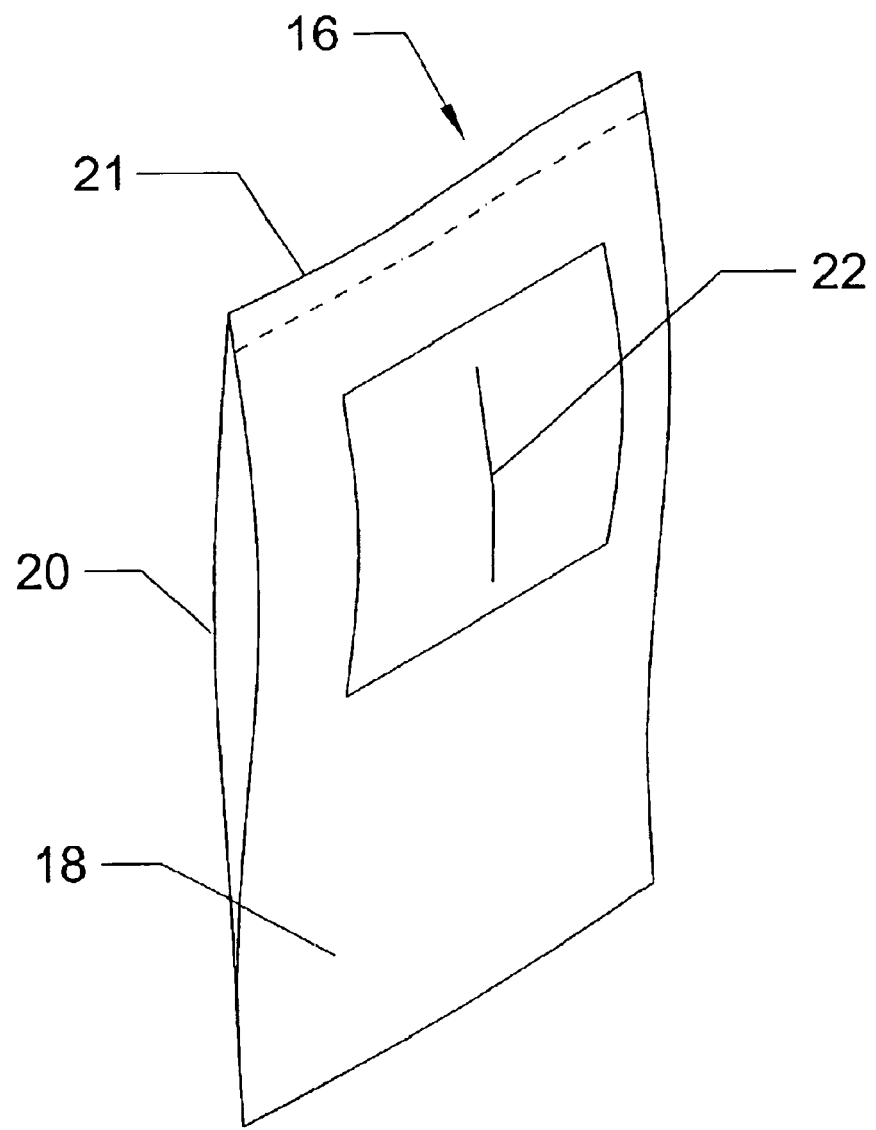
FIG. 3 depicts a perspective view of the inner bag.
Figure 4:
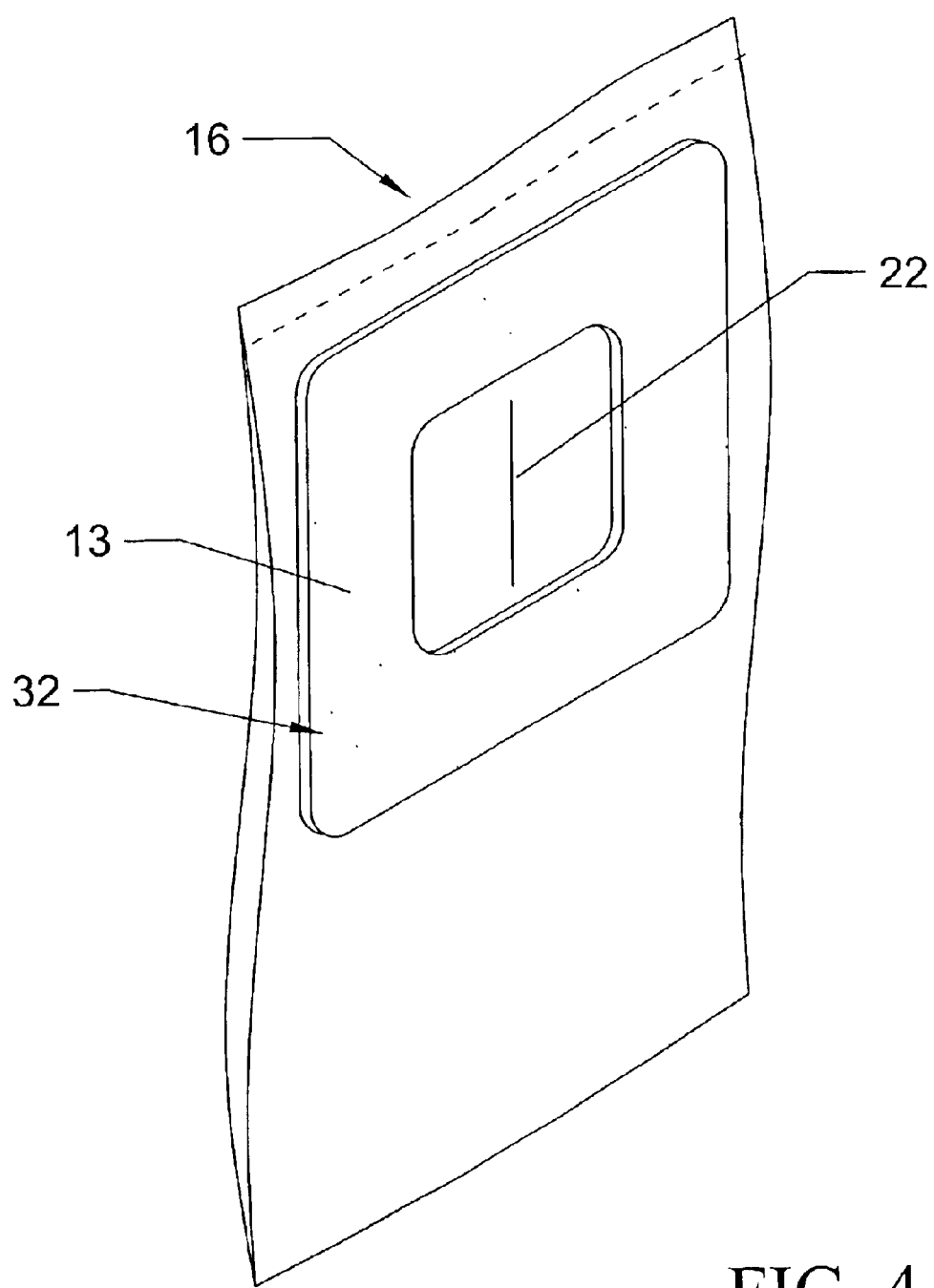
FIG. 4 depicts a perspective view of the inner bag with an annular ring.

FIGS. 2–4 illustrate an embodiment according to the present invention. The protective layer 14 includes an inner bag 16. A moisture resistant adhesive material 13 suitable for application to the patient's skin is applied to the peripheral edge 36 without discontinuity such that a protective seal can be formed to create an outer pocket 15 when the protective layer 14 is applied to the patient's skin. In this embodiment, the outer pocket 15 is substantially adhesive-free and can be of any size so long as the inner bag 16 is encompassed within the peripheral edge 36.

The inner bag 16 receives the proximal end of an implanted and/or transdermal medical device, having a front side 18 and a backside 20, where the front side 18 has an opening 22 therethrough. The inner bag 16 further comprises a moisture resistant adhesive material 13 suitable for application to the patient's skin, where the adhesive material 13 is applied to the outer surface of the front side 18 of the inner bag 16, substantially surrounding the opening 22, without discontinuity such that a protective seal can be formed when the inner bag 16 is applied to the patient's skin.

In an embodiment the inner bag 16 is rectangular, circular, elliptical, or other suitable shape.

In an embodiment the opening 22 is rectangular, circular, elliptical, or other suitable shape.

In an embodiment, a removable release layer covers the adhesive material 13, such that the implanted and/or transdermal medical device may be inserted into the inner bag 16 without adhering to the adhesive material 13.

In an embodiment, as shown in FIG. 2, the inner bag 16 is affixed to the protective layer 14, where the top edge 21 of the protected bag 16 is affixed to the protective layer 14.

In an alternative embodiment, as shown in FIG. 4, the inner bag 16 further comprises an annular ring 32, where the annular ring 32 is affixed about the opening 22 of the inner bag 16. The annular ring 32 is made of a flexible material capable of conforming to the surface of a patient's skin.

Figure 5:
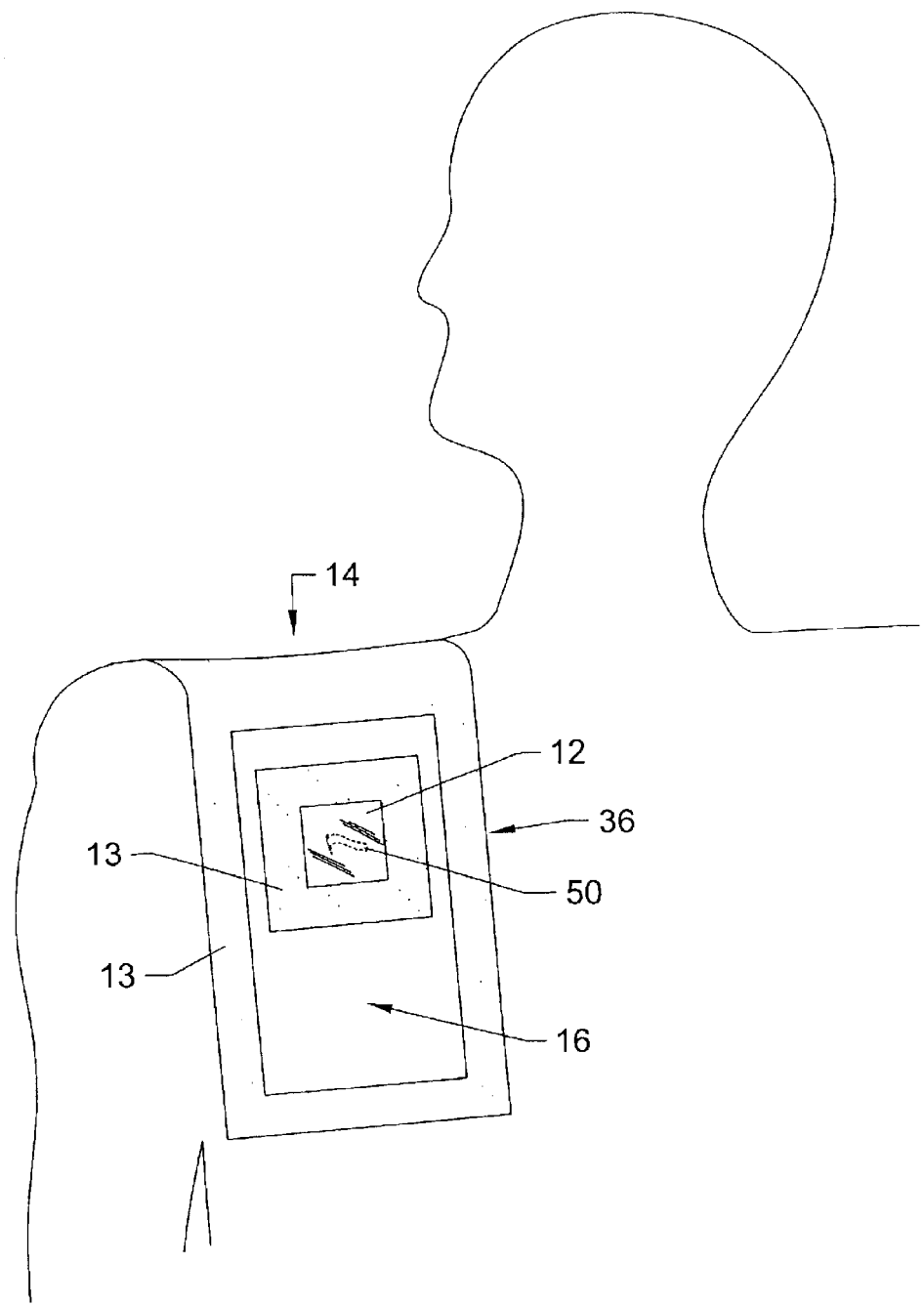
FIG. 5 depicts a perspective view of an implanted and/or transdermal medical device within the protective shield including an inner pocket.

In a method of use, as shown in FIGS. 1A and 5, the inner pocket 12 is placed over the implanted and/or transdermal medical device 50. The inner pocket 12 is secured in position by the adhesive material 13 contacting with the patient's skin forming a protective seal. The remaining portions of the protective layer 14 are applied over the skin of the patient, such that the inner pocket 12 is positioned within the peripheral edges 36 of the protective layer 14. The protective layer 14 is secured in position by the adhesive material 13 contacting the patient's skin, such that the protective layer 14 forms a protective seal and outer pocket about the inner pocket 12, protecting the inner pocket 12 from moisture, dirt, and debris.

Figure 6:
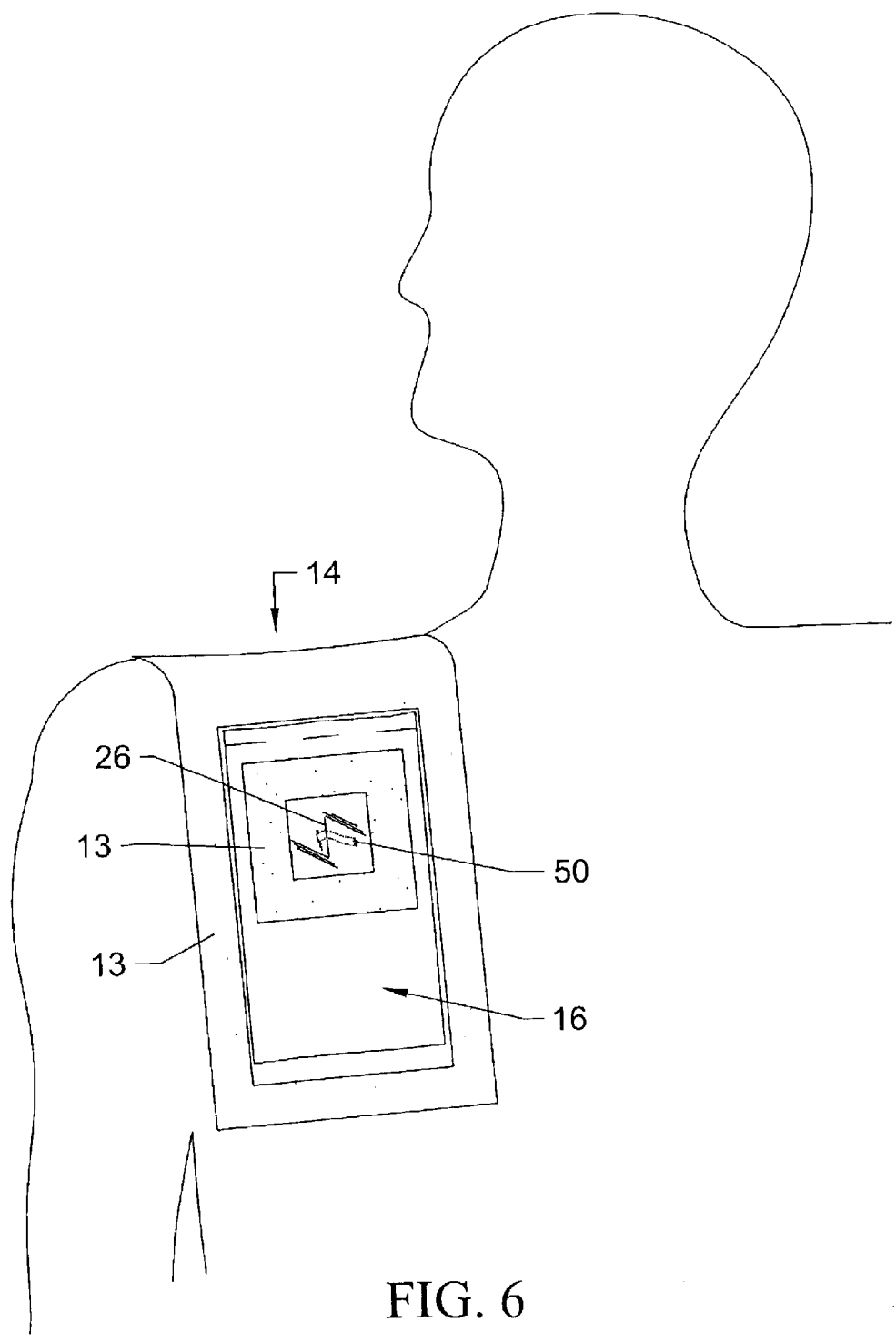
FIG. 6 a perspective view of an implanted and/or transdermal medical device within the protective shield including an inner bag.

In a method of use, as shown in FIGS. 2 and 6, an implanted and/or transdermal medical device 50 is inserted into the inner bag 16 by inserting the proximal end 51 of the medical device 50 though the slit 26 in the inner bag 16. The medical device 50 is drawn into the inner bag 16 until the outer surface of the front side of the inner bag 16 abuts the medical device 50 exit site and surrounding area. The inner bag 16 is secured in position by the adhesive material 13 contacting with the patient's skin forming a protective seal. The protective layer 14 is positioned over the inner bag 16, such that the inner bag 16 is positioned within the peripheral edges 36 of the protective layer 14. The protective layer 14 is secured in position by the adhesive material 13 contacting the patient's skin, such that the protective layer 14 forms a protective seal about the inner bag 16, protecting the inner bag 16 from moisture, dirt, and debris.

Following are examples which illustrate procedures for practicing the invention. These examples should not be construed as limiting. All percentages are by weight and all solvent mixture proportions are by volume unless otherwise noted.

EXAMPLE 1

Protective Shield in the Form of an Inner Bag and Outer Protective Layer

The protective shield consists of an inner plastic bag including an opening therethrough. On the front side, peripheral edges of the inner bag are a pattern of medical grade adhesive to attach the inner bag to the patient. The medical grade adhesive of the inner bag may be treated with appropriate agents to inhibit the development of bacterium, fungi, viruses, and other infectious agents. The inner bag is of adequate size to accept the end of a medical device exiting the body. The protective shield further comprises an attachable outer plastic protective layer that covers the inner bag, where the edge of the protective layer is surrounded with medical grade adhesive that adheres to the patient, diverting the flow of fluid away from the opening of the inner bag. The protective shield is designed to be used by patients with medical devices exiting their bodies while they shower, bath, swim or perform activities where the device exist site from the body is at risk of coming into contact with excessive fluid and/or debris.

The adhesive may be covered by a protective peel to allow the patient to insert the medical device through the opening into the inner bag, without the adhesive sticking to the patient, the protective layer, inner bag, or medical device. The protective peel is removed once the medical device is inserted through the opening and the inner bag is adhered to the skin. Similarly, once the inner bag is in position, the protective peel is removed from the protective layer and the protective layer is adhered to the skin, over the inner bag.

The protective shield provides two levels of protection for the medical device and exit site. The first level of protection is the protective layer, directing the flow of water and/or debris away from the inner bag. The second level of protection is the adhesive on the inner bag, which protects and seals the area surrounding the exit site.

EXAMPLE 2

Protective Shield in the Form of an Inner Pocket and Outer Protective Layer

The protective shield consists of a protective layer. The protective layer includes a moisture resistant adhesive material suitable for application to the patient's skin is applied to the peripheral edge of the protective layer without discontinuity such that a protective seal can be formed to create an outer pocket when the protective layer is applied to the patient's skin. The protective layer also includes an inner pocket that is formed by moisture resistant adhesive material disposed within the outer pocket. The moisture resistant adhesive material disposed within the outer pocket forms a continuous border around the area in which the implanted and/or transdermal medical device is located.

The protective layer is of adequate size to encompass within its peripheral edges an inner pocket that is sized to accept the end of a medical device exiting the body. The edge of the protective layer is surrounded with medical grade adhesive that adheres to the patient, diverting the flow of fluid away from the inner pocket pouch. The protective shield is designed to be used by patients with medical devices exiting their bodies while they shower, bath, swim or perform activities where the device exist site from the body is at risk of coming into contact with excessive fluid and/or debris.

The adhesive that forms the inner and outer pockets may be covered by a protective peel to allow the patient to position the protective shield over the medical device so that the medical device is positioned within the inner pocket, without the adhesive sticking to the patient, the protective layer, or medical device. The protective peel covering the adhesive that forms the inner pocket is removed once the medical device is properly positioned within the inner pocket. Similarly, once the inner pocket is secured over the medical device, the protective peel is removed from the adhesive that forms the outer pocket and the protective layer is adhered to the skin, over the inner pocket.

The protective shield comprising an outer pocket and an inner pocket provides two levels of protection. The first level of protection is afforded by the protective layer, which seals an outer pocket over the inner pocket and directs the flow of water and/or debris away from the inner pocket. The second level of protection is the adhesive that forms the inner pocket, which protects and seals the area surrounding the exit site against any moisture or debris that might have entered into the outer pocket.

It should be understood that the example and embodiments described herein are for illustrative purposes only and that various modifications or changes in light thereof will be suggested to persons skilled in the art and are to be included within the spirit and purview of this application and the scope of the appended claims.

I claim:

1. A protective shield for providing a moisture and debris resistant barrier surrounding an implanted and/or transdermal medical devices and exit site, comprising:

a) an inner bag having at least one opening for placement over the medical device and exit site, the inner bag further comprising first adhesive substantially surrounding the opening for attachment to the skin, such that a protective seal can be formed between the inner bag and the skin; and b) a protective layer comprising a flexible sheet having a second adhesive about a peripheral edge for adhering to the skin to form an outer pocket, wherein the outer pocket is an adhesive-free area that encompasses the inner bag such that the inner bag is sealed beneath said protective layer.

2. The protective shield according to claim 1, wherein the inner bag and the protective layer are made from a flexible, fluid impermeable material.

3. The protective shield according to claim 2, wherein the flexible, fluid impermeable material is plastic, polymer, silicon, vinyl, latex, or rubber.

4. The protective shield according to claim 1, wherein the inner bag and the protective layer are made from a material substantially impervious to infectious agents.

5. The protective shield according to claim 1, wherein the inner bag comprises an annular ring integrally formed with the opening.

6. The protective shield according to claim 1, wherein the protective layer comprises an annular ring integrally formed with the peripheral edge.

7. The protective shield according to claim 1, wherein the adhesive is a medical grade adhesive for application to the skin.

8. The protective shield according to claim 7, wherein the adhesive is a moisture resistant adhesive.

9. The protective shield according to claim 7, wherein the adhesive is treated to inhibit infection.

10. The protective shield according to claim 1, wherein the adhesive comprises a removable strip for protecting said adhesive prior to use.

11. The protective shield according to claim 1, wherein the inner bag is affixed to the protective layer.

12. The protective shield according to claim 1, wherein the protective layer is applied over a shoulder or around a waist or extremity.

* * * * *